(12) United States Patent
Fisher

(10) Patent No.: US 6,272,372 B1
(45) Date of Patent: Aug. 7, 2001

(54) NEEDLE HAVING INFLATABLE POSITION INDICATOR

(75) Inventor: John Fisher, Belleair, FL (US)

(73) Assignee: Biopsy Sciences, LLC, Clearwater, FL (US)

( * ) Notice: Subject to any disclaimer, the term of this patent is extended or adjusted under 35 U.S.C. 154(b) by 0 days.

(21) Appl. No.: 09/328,567

(22) Filed: Jun. 9, 1999

(51) Int. Cl.$^7$ .................................................. A61B 6/00
(52) U.S. Cl. ............................................................ 600/431
(58) Field of Search .................................. 600/431, 433, 600/434, 435, 466, 470, 550; 606/7, 116; 128/898

(56) References Cited

U.S. PATENT DOCUMENTS

| | | | |
|---|---|---|---|
| 5,301,682 | * | 4/1994 | Debbas ................................. 600/550 |
| 5,879,357 | * | 3/1999 | Heaton et al. ....................... 606/116 |

* cited by examiner

*Primary Examiner*—George Manuel
(74) *Attorney, Agent, or Firm*—Ronald E. Smith; Smith & Hopen, P.A.

(57) ABSTRACT

A guide needle for locating the position of a lesion or tumor in soft tissue has an inflatable balloon adjacent its pointed tip so that the position of the guide needle with respect to the lesion or tumor can be determined upon visual inspection of an ultrasound, CT scan, or other imaging technique when the balloon is inflated. A flexible bulbous reservoir positioned near a proximal end of the guide needle contains a saline solution or other suitable contrasting liquid fluid and is in fluid communication with the inflatable balloon through a tube. Squeezing the bulbous reservoir inflates the balloon and releasing the bulbous reservoir deflates the balloon. A clamp attachable to the proximal end of the tube is closed after the bulbous reservoir has been squeezed to lock the balloon into its inflated configuration when the guide needle is properly positioned relative to the lesion or tumor. The inflated balloon indicates the position of the guide needle and also anchors the guide needle into position. A biopsy tool is inserted into the guide needle to harvest samples of tissue from the lesion or tumor.

10 Claims, 4 Drawing Sheets

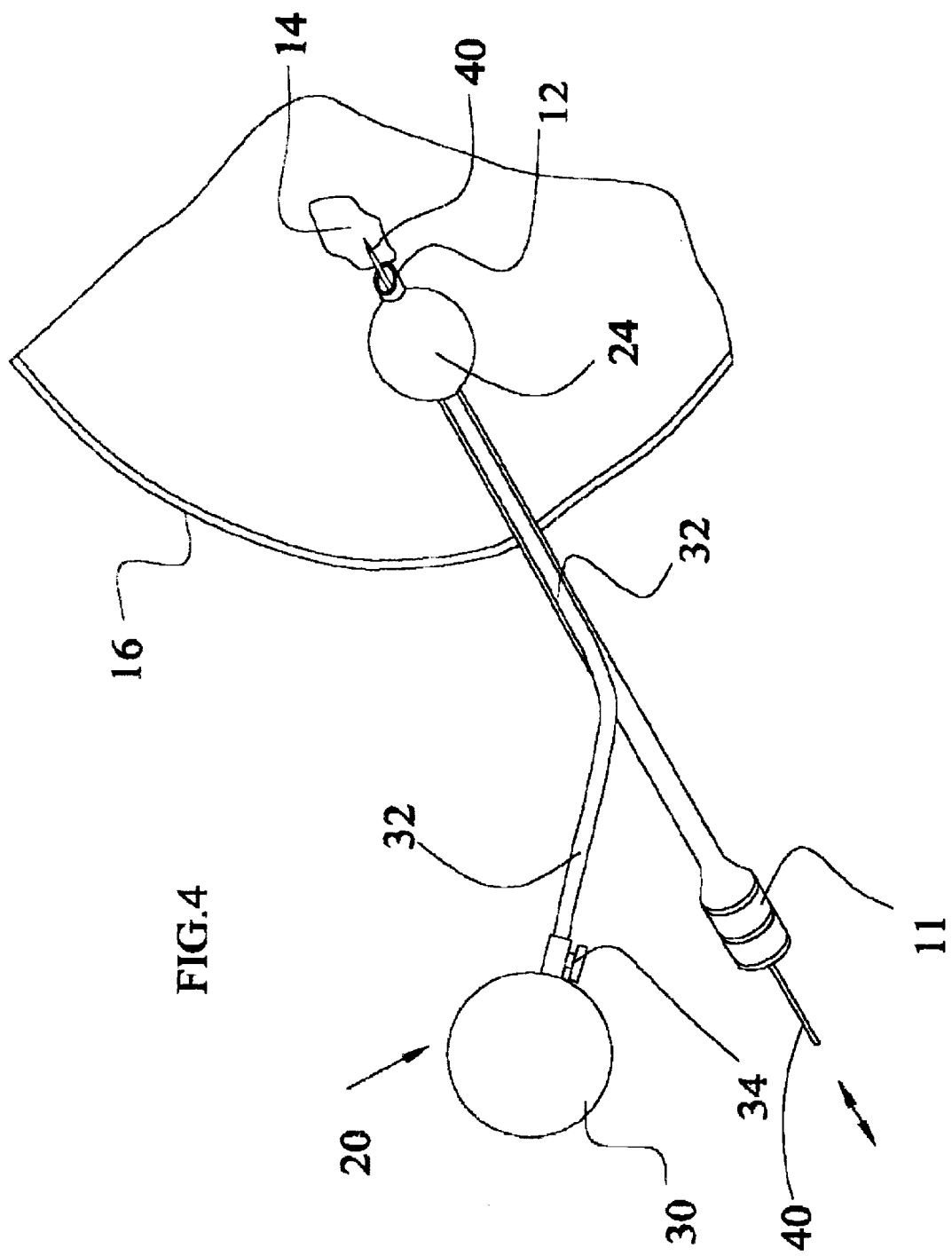

NEEDLE HAVING INFLATABLE POSITION INDICATOR

BACKGROUND OF THE INVENTION

1. Field of the Invention

This invention relates, generally, to tools used in radiology. More particularly, it relates to a biopsy tool that helps radiologists using imaging techniques such as ultrasound or CT scanning to properly align a guide needle relative to a lesion or tumor in a breast or other soft tissue.

2. Description of the Prior Art

One commonly used biopsy tool is a spring-loaded, trigger-operated device that shears off and captures a tissue sample from a lesion or tumor so that the sample can be analyzed in a lab. A guide needle is first inserted into a breast or other soft tissue where a lesion is detected, using a preselected imaging technique such as ultrasound or CT scanning, so that the physician can see the guide needle and the lesion. The longitudinal axis of the guide needle is aimed directly at the lesion, and the distal end or tip of the guide needle is placed in close proximity to the lesion. The proximal end of the guide needle remains external to the breast or other soft tissue.

If the guide needle appears to be properly positioned relative to the lesion, the leading end of the biopsy tool is then inserted into the bore of the guide needle at its proximal end. When the trigger is pulled, the operative part of the biopsy tool extends quickly, under the bias of its propulsion spring, from the open distal end of the guide needle, enters into the lesion, shears off a tissue sample, captures the sheared off sample in a small compartment, and retracts. The physician withdraws the biopsy tool from the guide needle, removes the sample from the compartment, and re-introduces the tool into the guide needle for the taking of an additional sample. A physician will typically take four of five such samples in sequence to ensure that different parts of the lesion have been sampled and to provide sufficient tissue for the testing lab. Using the guide needle requires but one entry into the breast or soft tissue and allows multiple entries of the biopsy tool through the hollow bore of the guide needle.

There are several drawbacks to this well-known procedure. First of all, it is difficult to see the guide needle under ultrasonic, CT scanning, and other types of imaging. If the guide needle is improperly positioned with respect to the lesion, the spring-loaded biopsy tool inserted thereinto will be equally mis-positioned and the tissue-shearing mechanism will miss the lesion when the trigger is pulled. The guide needle has a rather large bore to accommodate the biopsy tool, so the patient is not pleased when it has to be withdrawn and re-inserted so that the physician may try to hit the lesion again.

Nor does the art provide any means for preventing migration of the guide needle after it has been successfully positioned in an optimal relationship with a lesion or tumor. Thus, if a patient has had to endure numerous guide needle re-entries until it is finally properly positioned, a migration of the needle tip away from the lesion can still result in a missed biopsy because the shearing mechanism of the biopsy tool may fall short of the lesion and shear healthy tissue.

What is needed, then, is a means for enhancing the visibility of the guide needle under ultrasound, CT scanning, or other imaging technique. If such a means could be found, it would ensure proper alignment and optimal placement of the guide needle relative to a lesion or tumor and thus would ensure consistent hitting of the lesion by the shearing mechanism of the spring-loaded biopsy tool. Repeated insertions of the large bore guide needle would then become unnecessary.

A means for anchoring the guide needle into position after it has been optimally positioned is also needed.

However, it was not obvious to those of ordinary skill in this art how the needed means could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. The present invention includes an apparatus for properly positioning a guide needle in alignment and proper spacing relation to a lesion or tumor in a breast or other soft tissue mass.

The apparatus includes a hollow bore guide needle having a proximal end and a pointed distal end. An inflatable balloon means is secured to the guide needle adjacent the pointed distal end. The balloon means has a deflated configuration where its lies snugly against an exterior surface of the guide needle so that it does not interfere with insertion of the guide needle into a breast or other soft tissue. An inflation means is connected to the guide needle at the proximal end thereof for selectively inflating the balloon means, and the balloon means when inflated contains a preselected liquid fluid that is visible under ultrasound imaging or CT scanning when the balloon means is in its inflated configuration.

The inflation means includes a flexible, bulbous reservoir means for holding a predetermined amount of the preselected liquid fluid. An elongate tube means extends in fluid communication between the bulbous reservoir means and the balloon means so that the predetermined liquid fluid flows from the bulbous reservoir means into the balloon means when the bulbous reservoir means is compressed.

A locking means locks the balloon means into its inflated configuration. The locking means may be provided in the form of a clamp means that is attachable to a proximal end of the tube means. The clamp means has a closed position that prevents reverse liquid fluid flow through the tube means.

It is a primary object of this invention to advance the art of lesion or tumor biopsy.

A more specific object is to provide a means that enhances the visibility of a guide needle under ultrasound, CT scanning, or X-ray imaging.

Another object is to provide a means for anchoring a guide needle against movement.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 4 is a perspective view depicting a needle of a biopsy tool inserted into the novel guide needle where the trigger of such tool has been pulled so that the needle has momentarily entered into the lesion to shear off and capture a piece thereof.

DETAILED DESCRIPTION OF THE PREFERRED EMBODIMENT

Figure 1:
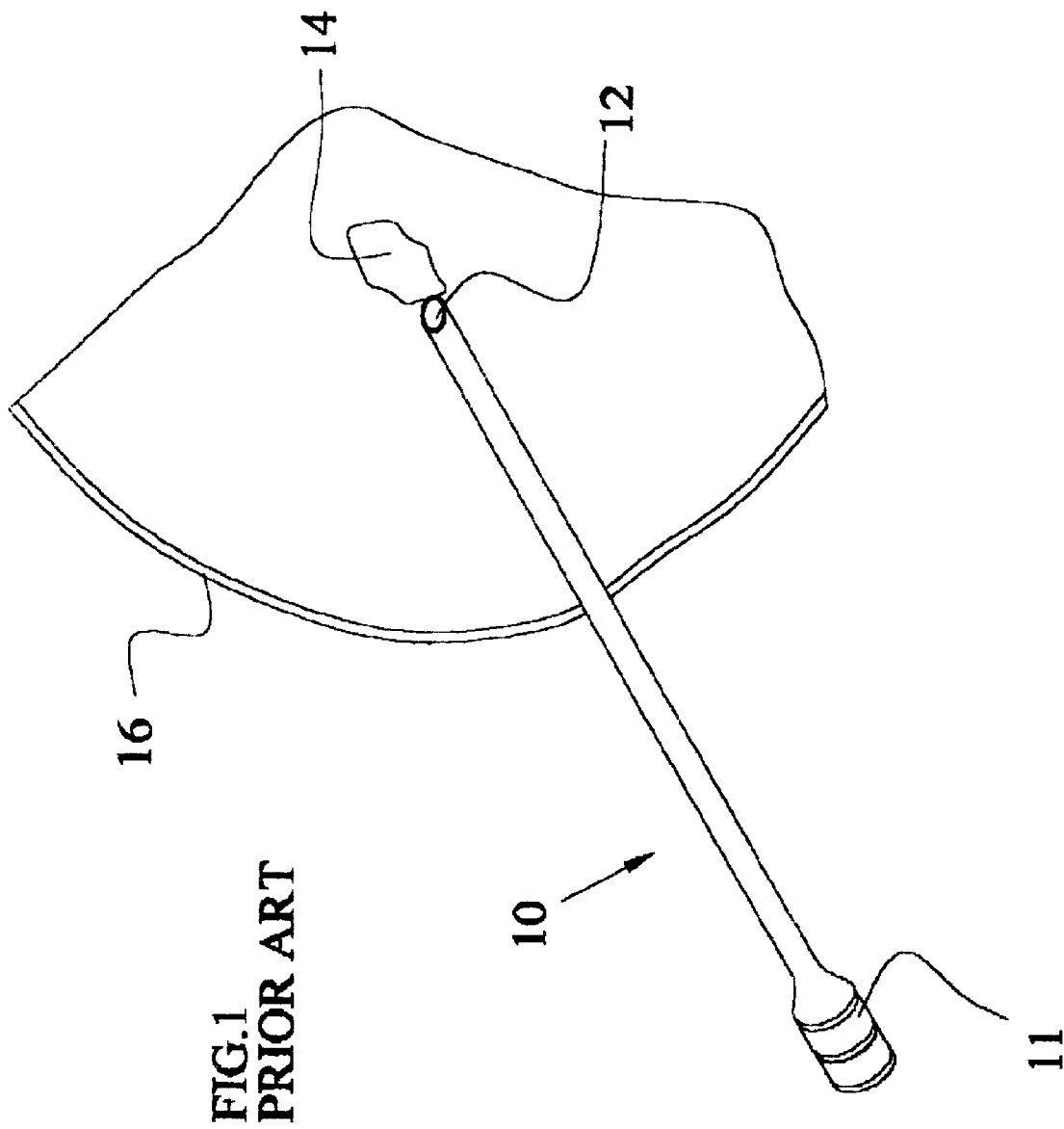
FIG. 1 is a perspective view of a guide needle of the prior art when inserted into a breast.

Referring first to FIG. 1, it will there be seen that a guide needle 10 of the prior art has a proximal end 11 and a pointed distal end or tip 12 and is positioned in longitudinal alignment with a lesion 14 in a breast 16. However, needle 10 and tip 12 are very difficult to see under imaging techniques such as ultrasound, CT scanning, X-rays and the like. Thus, guide needle 10 is easily mispositioned and might appear to be in proper alignment and spacing with lesion 14 when it really is not. Multiple attempts, each requiring re-entry of the needle and discomfort to the patient, may be needed to properly position a prior art guide needle.

Figure 2:
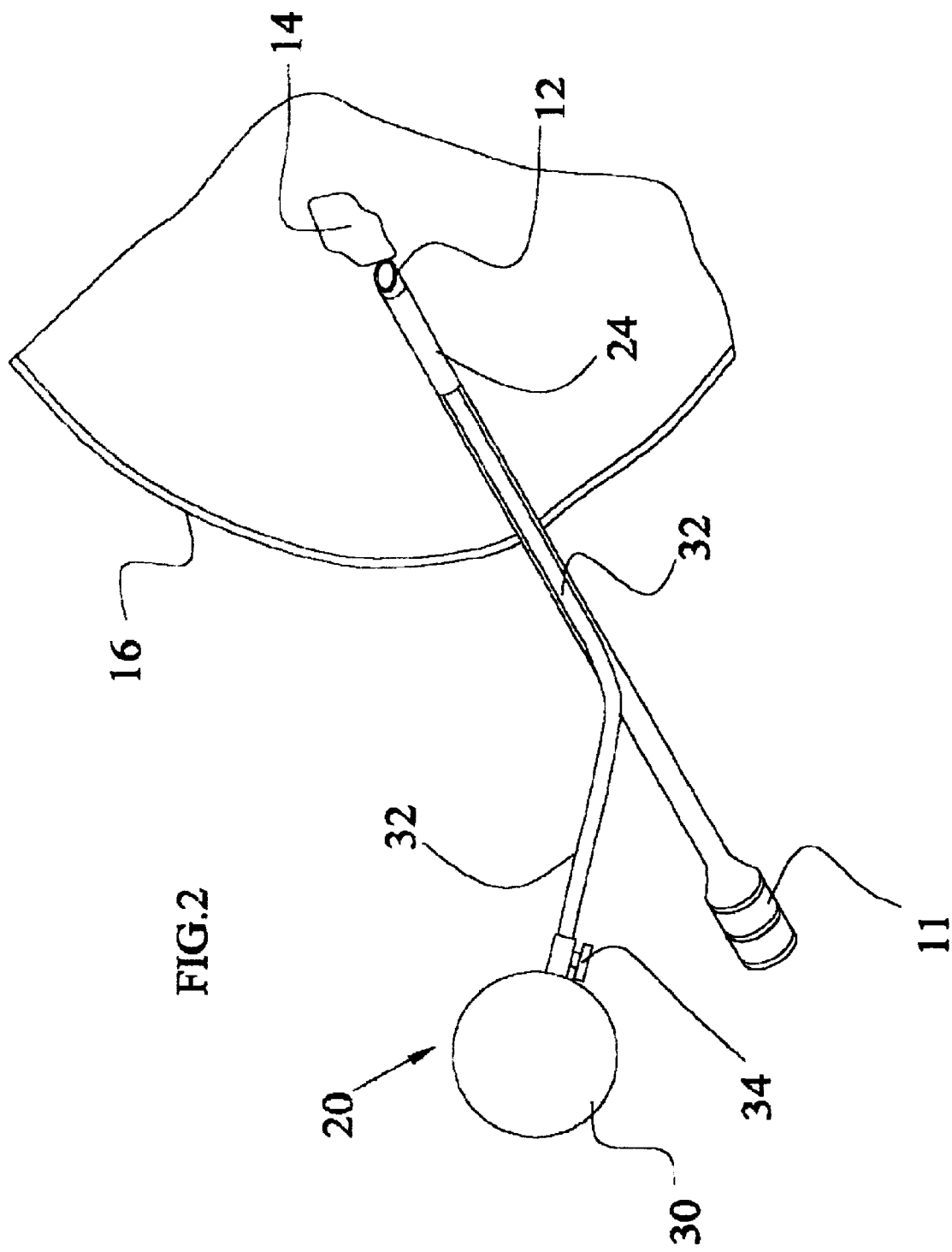
FIG. 2 is a perspective view depicting the guide needle of this invention inserted in a breast near a lesion with the balloon means in its deflated configuration.
Figure 3:
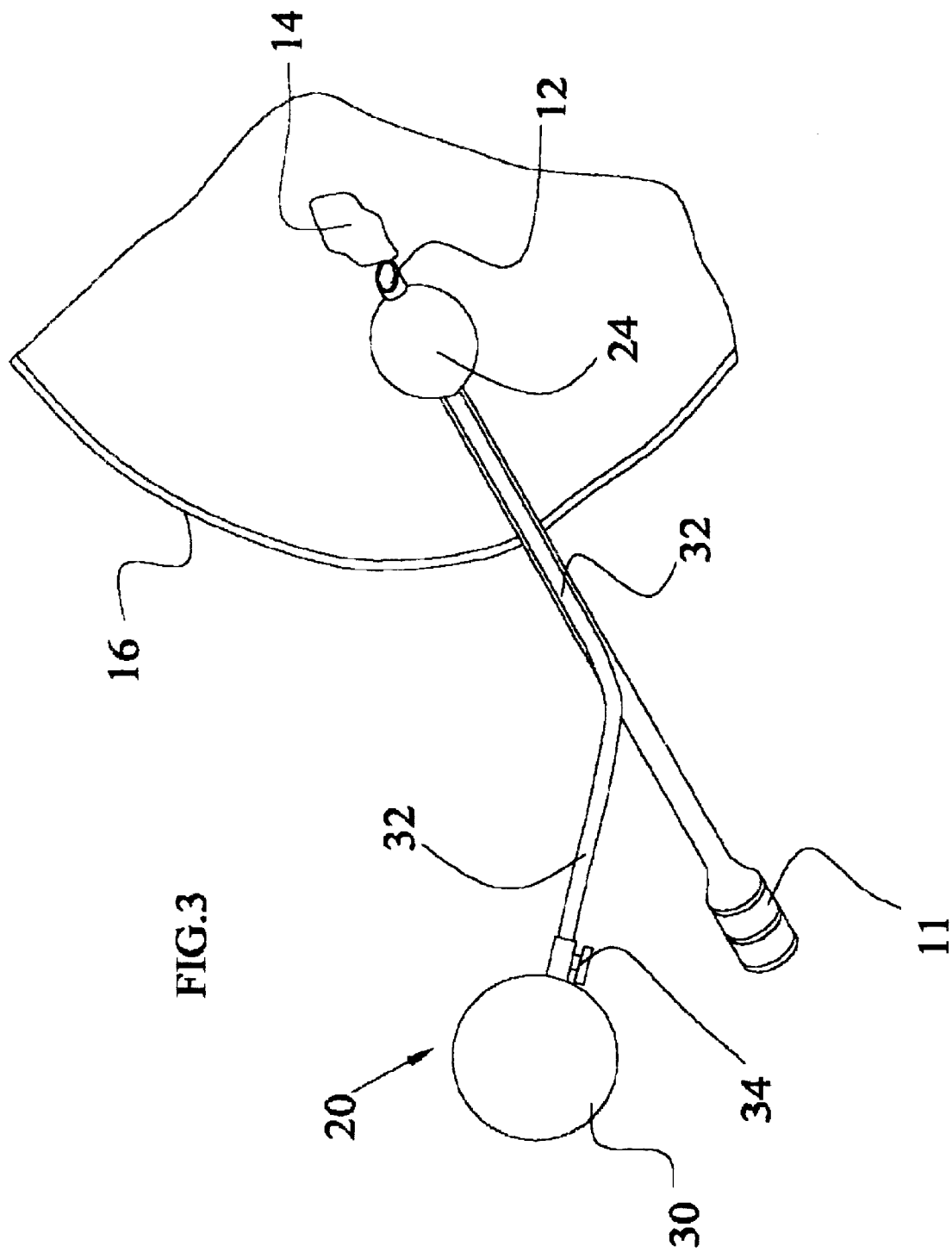
FIG. 3 is a perspective view depicting the novel guide needle with the balloon means in its inflated configuration.

Referring now to FIGS. 2–4, it will there be seen that an exemplary embodiment of the novel guide needle is denoted as a whole by the reference numeral 20. An inflatable balloon means 24 is positioned adjacent tip 12. Balloon means 24 is depicted in its deflated configuration in FIG. 2 and in its inflated configuration in FIG. 3.

Balloon means 24 is in its deflated condition when needle 20 is inserted into or withdrawn from the breast or other soft tissue. When so deflated, it lies snugly against the outer surface of guide needle in 10 as depicted in FIG. 2 and does not interfere with needle insertion.

Balloon 24 is inflated during the insertion while the procedure is monitored by ultrasonic or other preselected imaging means. As indicated in FIG. 3, when properly positioned, guide needle 20 is aimed directly at lesion 14 and tip 12 is in close proximity to the lesion. Significantly, it is the presence of the inflated balloon, filled with a suitable contrasting solution, which makes such proper positioning possible. The biopsy will be successfully completed when a spring-loaded, trigger-operated biopsy tool, not depicted in FIG. 3, is inserted into the hollow bore of guide needle 20 and the trigger of said tool is pulled, i.e., there is little or no chance that the shearing mechanism will miss its target as in the prior art.

If inflated balloon means 24 indicates that guide needle 20 is not aimed properly, balloon means 24 is deflated, the needle is withdrawn, and another attempt is made. If inflated balloon 24 indicates that tip 12 of guide needle 20 is too far from the lesion, the balloon is deflated, guide needle 20 is advanced, and the balloon is inflated again.

If inflation indicates that tip 12 is properly positioned, balloon means 24 is left in its inflated configuration to anchor guide needle, securing its position. The physician then uses guide needle 20 as a guide means for the spring-loaded biopsy device or other tool for harvesting samples of tissue from the lesion.

Balloon means 24 is not inflated with air because the balloon means has thin, clear walls; such walls and air are substantially invisible when viewed under ultrasound imaging. The preferred inflation medium is a saline solution or a contrast solution containing iodine or other ultrasound contrasting agent.

Although there are numerous mechanical means for effecting the inflation, the preferred means includes a manually-squeezeable bulb 30 that is in fluid communication with the proximal end of tube 32; the distal end of tube 32 is in fluid communication with the interior of balloon means 24. Bulb 30 is filled with saline solution or other suitable contrasting fluid that is easily visible under ultrasound imaging, CT scanning, and the like.

If inflation of balloon means 24 indicates proper alignment of guide needle 20 and proper spacing of needle tip 12 relative to the lesion or tumor, valve means or clamp 34 is closed to prevent reverse flow of the solution in said balloon so that said balloon remains in its inflated configuration. In addition to helping the physician see the placement of guide needle 20 and tip 12, inflated balloon means 24 also prevents migration of needle tip 12. Thus, it serves as an anchoring means as mentioned above.

FIG. 4 depicts a shearing needle 40 of a well-known biopsy tool inserted into the hollow bore of guide needle 20. More particularly, FIG. 4 depicts a brief moment in time when said needle 40 is propelled into lesion 14 by a spring, not shown, when a trigger, not shown, is pulled. The shearing action takes place very quickly and the unillustrated spring pulls shearing needle 40 quickly back into guide needle 20. With guide needle 20 in proper position, a physician may take several biopsy samples of the lesion in a few moments. Without the novel balloon, guide needle 20 may be mispositioned and the biopsy tool may miss the lesion and shear healthy tissue.

This invention represents a major breakthrough in the art of biopsy in general and guide needles in particular. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An apparatus for enabling a user to determine, through a preselected imaging technique, whether a pointed distal end of a guide needle is positioned adjacent to and in alignment with a lesion or tumor in soft tissue such as a breast, prior to taking a biopsy of said lesion or tumor, comprising:

a guide needle having a proximal end and a pointed distal end;

said guide needle having a bore of sufficient diameter adapted to accommodate a biopsy tool within said bore;

an inflatable balloon means secured to said guide needle adjacent said pointed distal end;

said balloon means having a deflated configuration where it lies snugly against an exterior surface of said guide needle so that it does not interfere with insertion of said guide needle into soft tissue;

inflation means connected to said guide needle at said proximal end thereof for selectively inflating said balloon means;

said balloon means when inflated containing a preselected liquid fluid that is visible under a preselected imaging technique when said balloon means is in its inflated configuration;

said balloon means when inflated serving as an anchoring means that prevents migration of the guide needle after the guide needle has been properly positioned relative to the lesion or tumor; and said balloon means when inflated facilitating visual observation of said pointed distal end of said guide needle under said preselected imaging technique so that it can be determined whether said pointed distal end is adjacent to and in alignment with said tumor or lesion;

said biopsy tool being inserted through said bore of said guide needle after said pointed distal end of said guide needle is determined by said visual observation to be adjacent to and in alignment with said lesion or tumor.

2. The apparatus of claim 1, wherein said inflation means includes a flexible, bulbous reservoir means for holding a predetermined amount of said preselected solution.

3. The apparatus of claim 2, further comprising an elongate tube means extending in fluid communication between said bulbous reservoir means and said balloon means so that said predetermined liquid fluid flows from said bulbous reservoir means into said balloon means when said bulbous reservoir means is compressed.

4. The apparatus of claim 3, further comprising: clamping means for locking said balloon means into its inflated configuration.

5. The apparatus of claim 4, wherein said locking means is a clamp means that is attachable to a proximal end of said tube means and wherein said clamp means has a closed position that prevents liquid fluid flow through said tube means.

6. The apparatus of claim 1, wherein said predetermined solution is a saline solution.

7. The apparatus of claim 1, wherein said predetermined solution is an ultrasound contrasting solution.

8. The apparatus of claim 1, wherein said preselected imaging technique is an ultrasound imaging means.

9. The apparatus of claim 1, wherein said preselected imaging technique is a CT scanning means.

10. The apparatus of claim 1, wherein said preselected imaging technique is an X-ray means.

* * * * *